(12) United States Patent
Steer et al.

(10) Patent No.: US 6,659,988 B1
(45) Date of Patent: Dec. 9, 2003

(54) OSTOMY APPLIANCE

(75) Inventors: Graham E. Steer, London (GB); Keith G. M. Hollands, W. Sussex (GB); Timothy K. Thorndale, Surrey (GB); Peter L. Steer, Sussex (GB)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/512,405

(22) Filed: Feb. 24, 2000

(51) Int. Cl.[7] .................................................. A61F 5/44
(52) U.S. Cl. ........................................ 604/333; 604/335
(58) Field of Search ................................ 604/332–345; 137/856, 855, 550; 383/100, 103

(56) References Cited

U.S. PATENT DOCUMENTS

| | | | | |
|---|---|---|---|---|
| 4,203,445 A | * | 5/1980 | Jessup et al. | 604/333 |
| 4,890,637 A | * | 1/1990 | Lamparter | 137/246 |
| 5,306,264 A | * | 4/1994 | Ferguson et al. | 604/333 |
| 5,401,264 A | * | 3/1995 | Leise, Jr. | 604/333 |
| 5,468,235 A | * | 11/1995 | La Gro | 604/333 |
| 5,690,622 A | * | 11/1997 | Smith et al. | 128/DIG. 24 |
| 5,690,623 A | * | 11/1997 | Lenz et al. | 604/332 |
| 6,056,439 A | * | 5/2000 | Graham | 383/103 |

\* cited by examiner

*Primary Examiner*—Weilun Lo
*Assistant Examiner*—C. Lynne Anderson
(74) *Attorney, Agent, or Firm*—Stuart E. Krieger

(57) ABSTRACT

An ostomy pouch (10) is described having an automatic pressure relief valve (82) which opens and closes automatically in response to the differential gas pressure across the valve to vent flatus. In one form, the valve comprises a diaphragm which seals against a seat by the use of a tacky gel or oil. The diaphragm is pinched towards one side and flexes as a flap.

In one preferred form, the valve (84) is used in combination with a deodorizing filter (82). The filter may be mounted co-axially with the valve, or it may be mounted separately and offset from the valve. A sub-envelope assembly (80) is described carrying the valve (84) and the filter (82) and defining a buffer volume between the valve and filter to compensate for the different flow characteristics of the valve and filter.

2 Claims, 5 Drawing Sheets

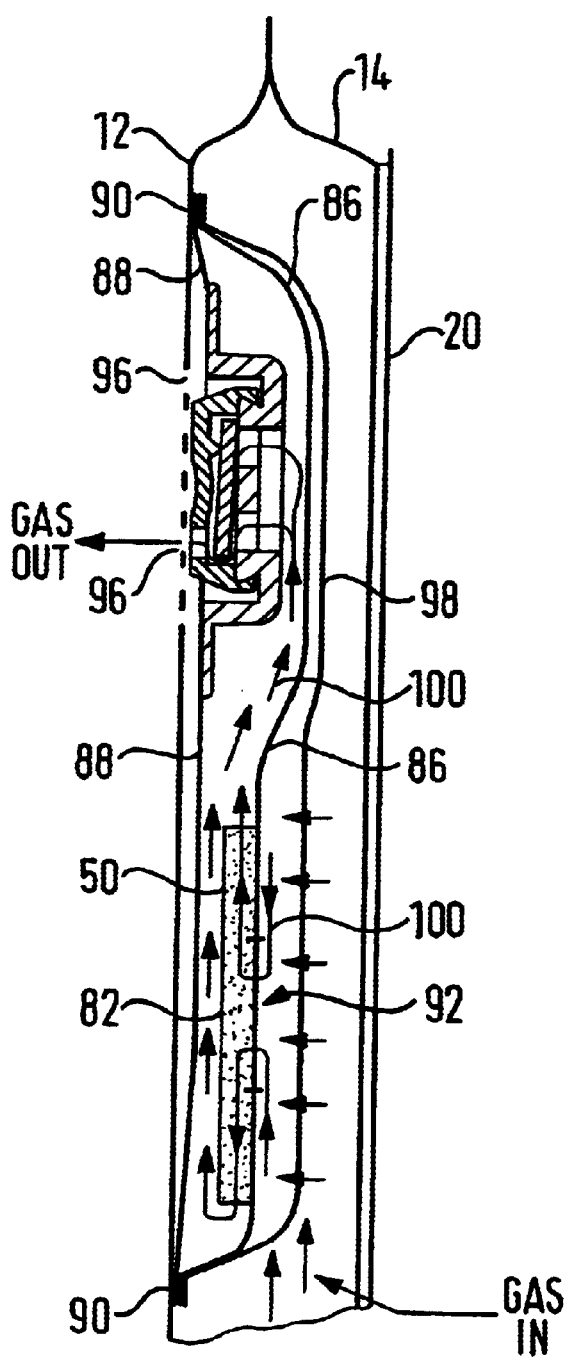
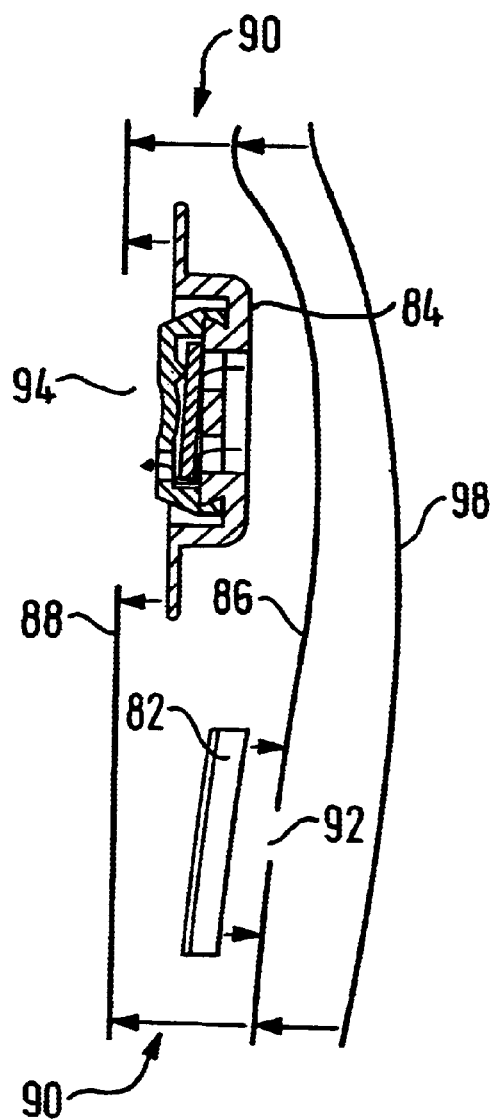
FIG. 6
FIG. 7

OSTOMY APPLIANCE

This invention relates to an ostomy appliance, in particular to a filtered pressure relief vent for an ostomy appliance, for example, an ostomy pouch.

The term ostomy includes at least colostomy, ileostomy and urostomy.

Flatus vents have been provided on ostomy pouches to allow flatus gas to escape from the pouch, and hence prevent ballooning of the pouch. However, it is generally desired not to allow all of the gas within the pouch to escape, as this can cause the pouch to collapse against the wearer's stoma (a problem referred to as pancaking). Such collapsing can be very painful for the wearer, and can also obstruct the passage of faecal matter through the stomal aperture.

It is in practice very difficult to engineer the flow rate characteristics of a filter to achieve adequate flow to prevent ballooning while also avoiding the risk of pancaking. The amount of flatus produced by a person varies widely from one individual to another, and is also dependent on the person's diet and health.

There have been proposals in the art to fit pressure relief valves to ostomy pouches to regulate automatically the gas pressure within the pouch. Such proposals are described, for example, in U.S. Pat. No. 3,865,109, GB 2094153 and GB 2122499. However, to date, such designs have not found commercial acceptance in ostomy products. It is believed that problems in one or more of the following areas might have made the designs impractical for large scale production: reliability; reproducibility; difficulty of manufacture; size; and cost.

Therefore, there remains a significant need for an automatic pressure relief vent which overcomes the problems of the prior art.

Broadly speaking, one aspect of the present invention is to provide a pressure relief valve for an ostomy pouch, the valve having one or more of the following characteristics:

(a) The valve includes a movable diaphragm, at least one of the diaphragm and its seal seat comprising or carrying a sticky and/or tacky and/or oily and/or greasy material. Such a feature can ensure that a reliable seal is formed between the diaphragm and the seal seat to prevent unwanted leakage at low pressures, without requiring a strong bias to hold the diaphragm against the seal seat.

(b) The valve includes a movable diaphragm (or diaphragm) which is pinched or held at, or towards, a first edge region of the diaphragm, leaving a generally opposite second region of the diaphragm unhindered. The diaphragm functions as a flap. Such a feature can enable the size of the valve to be reduced, compared to more conventional rotationally symmetric proposals known in the prior art.

The resistance offered by the flap will be affected by characteristics including the stiffness of the diaphragm material, the size and thickness of the diaphragm, and the position and size of the means for gripping or pinching the fixed region of the diaphragm. These factors can be engineered to achieve suitable pressure responsive characteristics. For example, for a given size of diaphragm, and a given diaphragm material, it is still possible to control the pressure at which the diaphragm opens by selecting an appropriate fixed grip position of the diaphragm about which the diaphragm has to bend to open.

(c) The valve includes a deformable (preferably bendable) diaphragm (or diaphragm) having a thickness/lateral dimension ratio of not significantly less than about 1/30 (i.e. not significantly less than 0.03). Preferably, the ratio is larger and, with increasing preference for larger ratios, is at least about 1/20, 1/15, 1/12, 1/10, 1/9, 1/8 and most preferably at least 1/7. If the diaphragm has more than one lateral dimension (e.g. if not circular), then the above ratio should apply to at least the smallest lateral dimension. Such a feature may enable more consistent characteristics to be achieved, and is in contrast to relatively thin bendable diaphragms suggested in the prior art.

(d) The pressure at which the valve opens is less than about 0.15 psig, and preferably is less than about 0.1 psig. (The term psig refers to psi "gauge", and indicates a positive pressure differential across the valve, i.e. a positive pressure inside the pouch relative to external atmospheric pressure outside the pouch).

(e) The valve diaphragm is protected from direct contact with liquid and/or solid stomal discharge, by means of a protection layer which is of a material, or is so arranged, to act as a barrier (or obstacle) to liquid, while permitting the flow of gas. For example, the protection layer may consist of microporous PTFE.

(f) The valve unit comprises a diaphragm which precedes the or a filter material.

(g) The valve includes a filter which selectively blocks the passage of certain gases (including selected unpleasant odorous gases) such that those gases remain trapped within the pouch. Such a feature is in contrast to many conventional ostomy filters which adsorb the unpleasant gas molecules within the filter.

(h) The valve comprises a casing containing a movable diaphragm (or diaphragm), the case comprising a first part securable to the pouch and defining a well for receiving the diaphragm, and a second part receivable within the well to cover the diaphragm. Preferably, the second part is dimensioned to be received substantially entirely within the well. Preferably, the second part is secured to the first part by a mechanical interlock. Preferably, the second part comprises an outlet aperture for allowing gas escaping past the diaphragm to exit from the casing.

(i) The valve is or comprises a so-called coffee-bag-type vent. Such vents are known in the very different field of coffee packaging, to allow excess pressure to be relieved from packets of coffee. Designers in that field are faced with different technical problems from those discussed above. In particular, one problem is how to preserve the pleasant aroma of the coffee, in contrast to the problem in the ostomy field of how to quash unpleasant odours to which the human nose is highly sensitive. To the best of the inventor's knowledge, it is not known hitherto to use such a valve in the ostomy field.

An example of a so-called coffee-bag-type vent is described in EP-A-0659657.

In a second aspect, the invention provides an envelope (or sub-envelope) for use in an ostomy pouch, the sub-envelope having first and second apertures, a deodorising filter communicating with the first aperture and a pressure relief valve communicating with the second aperture, the envelope defining a buffer chamber for gas between the deodorising filter and the pressure relief valve.

Preferably, the envelope is inflatable at least to some extent.

Preferably, the deodorising filter is secured to the envelope wall in a region around the first aperture.

Preferably, the pressure relief valve is secured to the envelope wall in a region around the second aperture.

The first aperture may be an inlet aperture for gas entering the sub-envelope, and the second aperture may be an exit aperture for venting gas externally. Alternatively, the functions of the apertures may be swapped.

Preferably, the pressure relief valve is of a type which opens automatically when a desired threshold pressure is reached.

In a third aspect, the invention provides an ostomy pouch comprising a pressure relief valve and a deodorising filter, the deodorising filter being offset from the pressure relief valve.

Preferably, the deodorising filter does not overlap the pressure relief valve. This can allow the filter element and the pressure relief valve to be mounted in a minimum profile height, to avoid increasing the thickness of the ostomy pouch unnecessarily.

Preferably, the deodorising filter is spaced from the pressure relief valve.

Preferably, the deodorising filter and the pressure relief valve are mounted on a sub-envelope within the pouch. Preferably, the sub-envelope defines a buffer chamber for gas between the deodorising filter and the pressure relief valve.

In a further aspect, the invention provides an ostomy appliance comprising any of the aforesaid arrangements. Preferably, the appliance is an ostomy pouch.

Embodiments of the invention are now described by way of example only, with reference to the accompanying drawings, in which:

FIG. 6 is a schematic section showing in more detail the sub-envelope used within the pouch of FIG. 5; and FIG. 7 is a schematic exploded view of the sub-envelope of FIG. 6.

Figure 1:
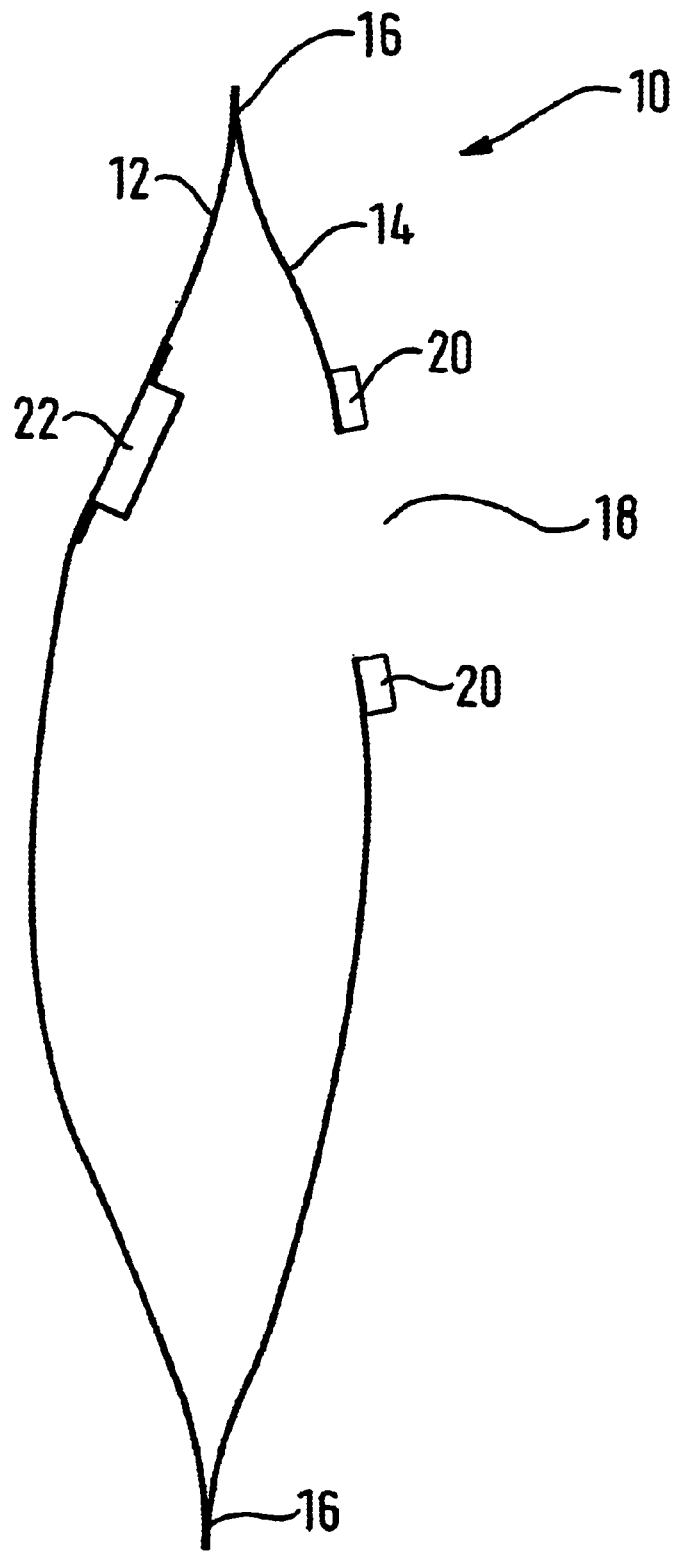
FIG. 1 is a schematic sectional view of an ostomy pouch with a pressure relief valve.
Figure 2:
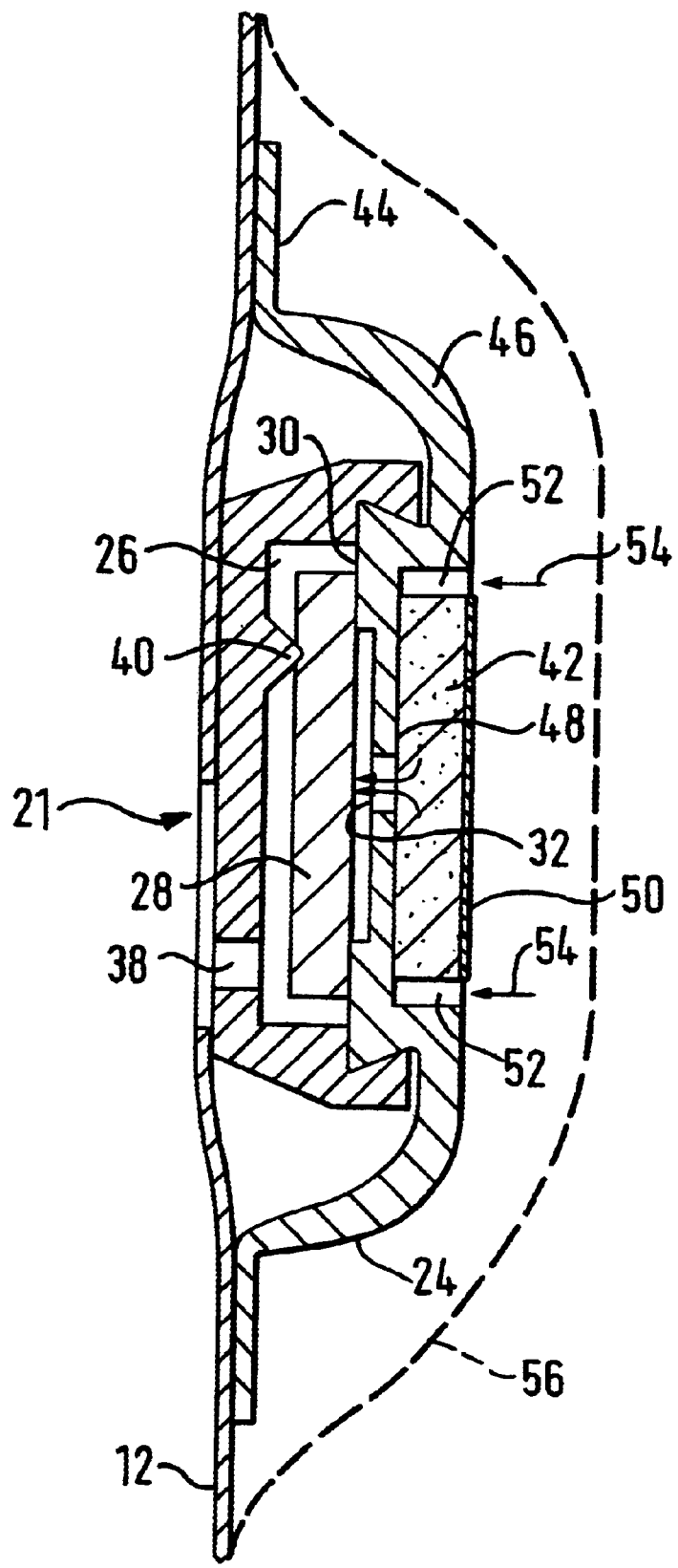
FIG. 2 is a schematic section showing the pressure relief valve in more detail.
Figure 3:
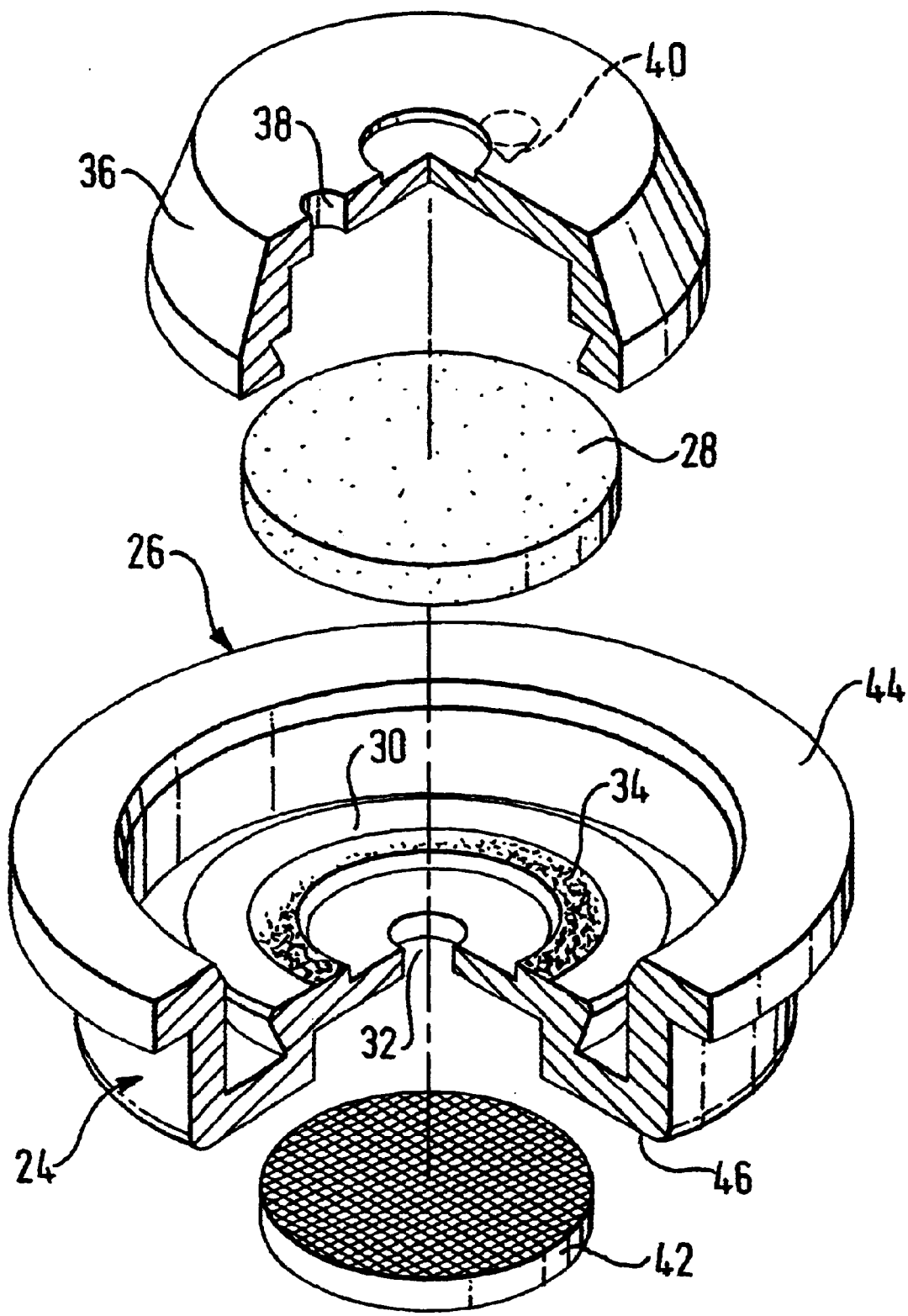
FIG. 3 is a perspective exploded view of the valve of FIG. 2.

Referring to FIGS. 1–3 of the drawings, an ostomy pouch 10 consists of a front wall 12 and a rear wall 14 welded together around their common periphery 16 to form a pouch envelope. The rear wall 14 is formed with a stomal aperture 18, and is secured to an attachment member 20 (depicted schematically). The attachment member 20 may, for example, consist of an adhesive annulus, or it may consist of a mechanical coupling ring for forming a mechanical interlock with a complementary bodyside member (not shown). Such attachment members are known in the art, and need not be described in detail here.

The front and rear walls 12 and 14 consist of material which is generally impervious to gas. For example, a typical ostomy pouch wall material may consist of one or more layers of ethylene vinyl acetate (EVA), a central gas barrier layer of polyvinylidine chloride (PVDC), and one or more inner layers of EVA.

The pouch 10 is also fitted with a filtered pressure release valve 22 which, in this embodiment, is on the front wall 12 of the pouch. It will be appreciated that, in other embodiments, the valve could be fitted to the rear wall 14 if desired. The pouch wall material is formed with a slit 21 (for example an S-cut or a X-cut) or other aperture to allow the escape of gas through the valve. The valve 22 has two purposes as follows:

(a) To open automatically when the gas pressure within the pouch exceeds a certain threshold, to thereby vent any "over pressure" within the pouch and avoid ballooning; and (b) To remain closed when the gas pressure in the pouch is below, or falls below, the threshold. This can maintain a controlled, partial inflation of the pouch and thereby avoid the pancaking problems discussed previously.

In the present embodiment, the threshold pressure is less than about 0.15 psig, and preferably is less than about 0.1 psig. However, higher pressure thresholds may be used if desired, according to particular desired pouch characteristics.

Referring to FIGS. 2 and 3, a first case member 24 defines a hollow well 26 for housing a bendable diaphragm 28. The floor of the well 26 includes a raised portion 30 having one or more through apertures 32, and also defining (or carrying) a seal seat 34 for the diaphragm 28. The seal seat 34 is defined by a layer of tacky, sticky, oily or greasy material, to form a reliable seal with the diaphragm 28. In the present embodiment, the seat material 34 comprises a thin layer of silicon gel or oil. It will also appreciated that, in other embodiments, this seat material could be provided on the diaphragm itself. The diaphragm may be made a solid piece of material, or it may be formed as a laminate.

The diaphragm 28 is held in position by means of a cap 36 which is received substantially entirely within the well 26. The cap has undercut edges which form a snap fit with complementary edges of the raised floor portion 30.

The upper wall of the cap is formed with a gas outlet aperture 38, and a projection 40 for bearing on the diaphragm 28 at, or towards one edge of the diaphragm. The diaphragm is trapped at the point of contact of the protrusion 40, and thus acts as a bendable flap. The pressure at which the diaphragm 28 opens depends on characteristics including the stiffness of the diaphragm material, the size and thickness of the diaphragm, and the position of the protrusion 40, which defines the "pivot" position about which the diaphragm bends in order to open.

The lower region of the case member 24 is formed with a recess for receiving a filter element 42. The filter element may consist, or include, charcoal or activated carbon. The purpose of the filter is to absorb the unpleasant odours in the gas passing through the filter, or to block (i.e. bounce back) such odours, depending on the filter characteristics.

Although an axial flow filter may be used, it is preferred that the filter element 42 be of a radial flow type. One surface 48 of the filter element 42 is welded or hot-melt sealed to the floor of the casing 24, and the other surface is sealed by a gas and liquid impermeable layer of plastics film 50. Gas enters the filter through the circumferential annular gap 52 around the filter (as depicted by arrows 54), passes radially through the filter material, and leaves the filter through the central aperture 32.

The material of the filter element may be coated to protect the filter from contact with solid and/or liquid matter collected within the pouch. Additionally, or alternatively, a gas permeable, liquid impermeable sheet (shown in phantom at 56) may be provided over the inlet to the filter.

The filter element itself also serves to protect the diaphragm 28 from becoming blocked, or wedged open, by solid or semi-solid matter becoming trapped in the valve.

In use, at relatively mild pressures inside the pouch, the combination of the tacky seal between the diaphragm 28 and the seal seat 34, stiffness of the diaphragm material, and the pressure applied by the projection 40 ensures that the valves remain closed, so that gas cannot escape through the valve.

When the internal pressure increases above the predetermined threshold (determined by the engineering, and material parameters, of the valve), the pressure is sufficient to lift the free edge of the diaphragm 28, and allow the gas to vent between the diaphragm 28 and the seal seat 34, and escape through the outlet aperture 38.

When the pressure subsequently falls below the threshold, the diaphragm returns to its sealing position against the seal seat 34, to thereby close the valve.

In this embodiment, the diaphragm 28 is relatively thick, and has a thickness/lateral dimension (diameter) ratio of about 1/7. It is believed that, by using such a relatively thick diaphragm made of relatively soft material, e.g. soft rubber, then the variational tolerances of the valve design can be improved compared to conventional designs using relatively thin bendable diaphragms.

In the illustrated embodiment, the valve is secured to the interior face of the pouch wall, by being welded around the outer rim 44. However, it will be appreciated that in other embodiments, the valve could be mounted on the exterior face of the pouch wall, for example, by being welded around the opposite surface 46.

Figure 4:
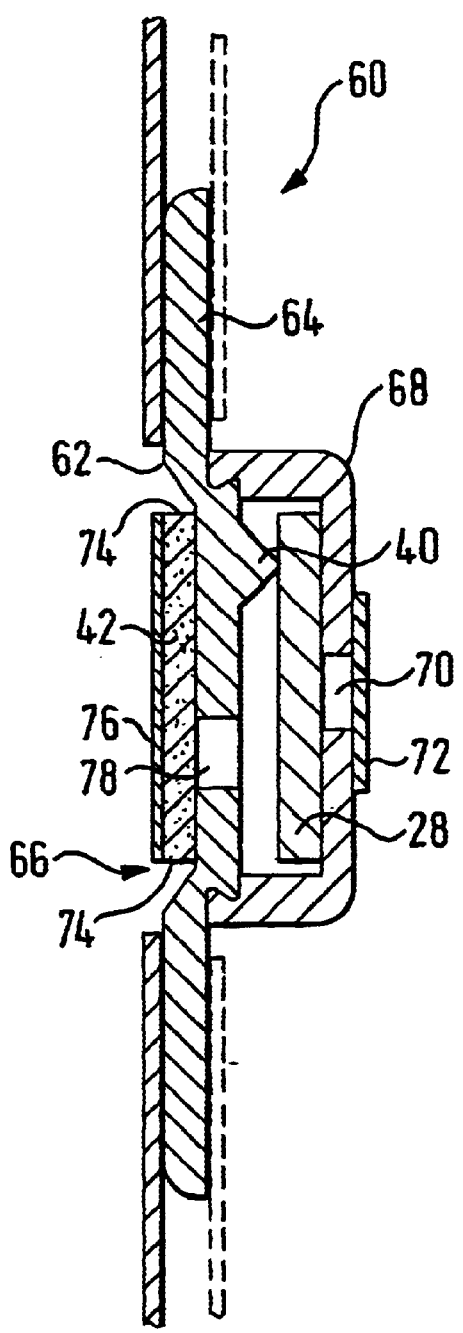
FIG. 4 is a schematic sectional view through a second embodiment of valve.

FIG. 4 illustrates a second embodiment of pressure relief valve 60. Where appropriate, the same reference numerals are used to denote equivalent features to those described previously. The second embodiment is very similar to the first except that, instead of preceding the diaphragm 28, the filter element 42 is located downstream of the diaphragm 28.

Referring to FIG. 4, the case consists of a first member 62 defining a flange 64 and a shallow well 66, and a second cup-shaped member 68 defining the recess for the diaphragm 28. The cup-shaped member has an entry aperture 70 protected by a film 72 of gas-permeable water impermeable material, for example PTFE. The first member 62 carries the projection 40 for pinching the diaphragm against the seal seat (defined by the second member 68).

The valve functions in exactly the same manner as that described previously, the diaphragm lifting along one edge when the pressure at the inlet exceeds the predetermined threshold. The gas then passes towards the filter element 42 through an aperture 78.

The filter element 42 is received in the shallow well 66 and is glued or heat-sealed to the first member 62. As in the first embodiment, the filter element 42 is a radial flow type element, such that gas passes in a radially outward direction to exit the filter around the circumferential edge 74. The radial flow is forced by a gas impermeable cover film 76.

The valve can be welded to the interior face of the pouch wall 12 (as illustrated in FIG. 4), or it could be welded to the exterior face of the pouch wall 12 (as depicted in phantom). With the latter design, the flange 64 would appear on the outer surface of the pouch wall, with the remainder of the valve assembly being recessed into the pouch.

Figure 5:
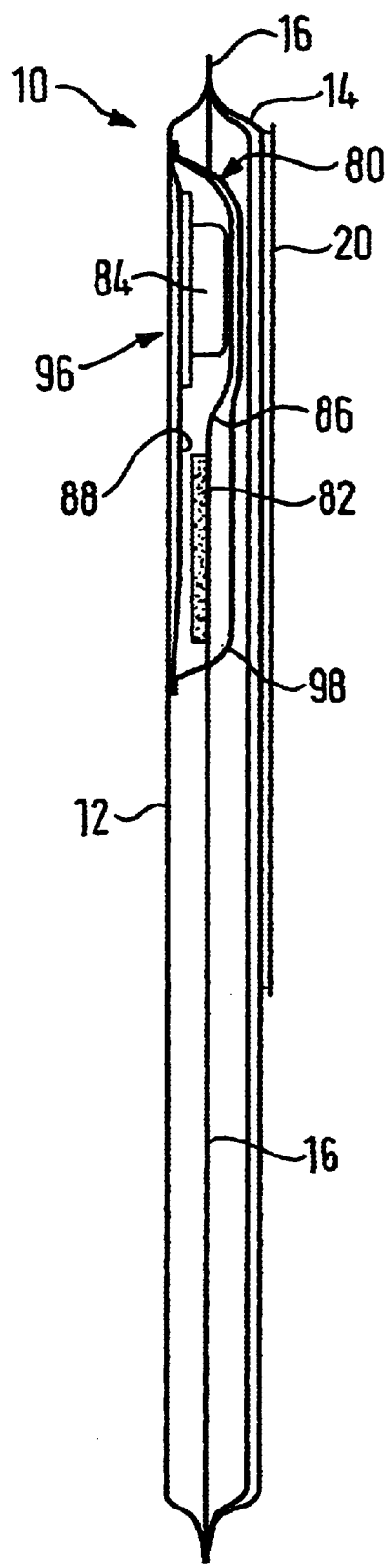
FIG. 5 is a schematic section of a further embodiment of an ostomy pouch with a pressure relief valve.

Although the above embodiments illustrate a combined co-axial filter and vent assembly, it will be appreciated that the same principles could also be applied to an ostomy appliance in which the pressure relief valve, and the filter, are not integrally mounted as a common unit, but are separately mounted relative to each other, as shown in FIGS. 5–7.

Referring to FIGS. 5–7, a further embodiment of ostomy pouch 10 is shown. Where appropriate, the same reference numerals are used to denote equivalent features to those described previously. In contrast to the previous embodiments employing co-axial filter and valve units, in the present embodiment, a sub-envelope 80 is shown in which the filter element 82 (42) is offset from the valve unit 84 (22).

The sub-envelope 80 consists of first and second impermeable plastics sheets 86 and 88 welded together around their common periphery 90. The sheets 86 and 88 may be of the same material as the front and rear walls 12 and 14 of the main pouch 10. The first sheet 86 has an entrance aperture 92 to allow gas to enter the sub-envelope 80, and the second sheet 88 has an exit aperture 94 which communicates with a vent outlet 96 in the front pouch wall 12.

As best seen in FIGS. 6 and 7, the filter element 82 is bonded to the first sheet 86 in a region surrounding the entrance aperture 92, such that gas entering the sub-envelope 80 is deodorised by the filter element 82. In a similar to that described previously, the filter element 82 carries a gas impermeable layer of plastics film 50 in order to ensure radial gas flow in the filter.

The valve unit 84 is offset from the filter element 82, and is bonded to the second sheet 88 of the sub-envelope 80 in a region surrounding the exit aperture 94. The valve unit may have the same constructional features as described in the previous embodiments (omitting the co-axial filter).

In this embodiment, the filter unit 82 is located within the sub-envelope 80, for optimum protection of the filter from faecal matter. However, it will be appreciated that, if desired, the filter element could be bonded to the first sheet 86 outside the sub-envelope 80. With either arrangement, it is preferred that a protection sheet 98 be bonded over the sub-envelope. The protection sheet is substantially gas permeable/liquid impermeable, and may for example comprise a microporous laminate. In a similar manner, the valve unit 84 could be bonded to the second sheet 88 outside the sub-envelope 80. In use, as shown by the arrows 100 in FIG. 6, flatus passes through the protection sheet 98 and into the sub-envelope via the entrance aperture 92. The flatus flows radially through the deodorising filter 84 and into the main volume of the sub-envelope 80. When the gas pressure within the sub-envelope has risen to a predetermined threshold the vent unit 84 opens automatically to vent the gas and release the built-up pressure.

It will be appreciated that the sub-envelope 80 provides an intermediate collection volume, or buffer volume, between the filter element 82 and the valve unit 84. This can reduce the contrary flow rates effects of the filter element 82 and the valve unit 84 on each other. In particular, the resistance of the filter element limits the flow rate through the filter and hence limits the ability to maintain a pressure behind the valve unit 84 once the valve unit 84 opens. Without a buffer volume, this might lead, in some cases, to erratic, intermittent opening and closing of the valve unit 34, and undesirable turbulent gas flow through the filter element 82. However, it is believed that the presence of a buffer volume can smooth the gas flow characteristics and avoid such a problem.

It is emphasised that the foregoing description is merely illustrative of a preferred form of the invention, and that many modifications can be made within the scope and/principles of the invention.

Features believed to be particular importance have been identified in the foregoing description. However, the applicant claims protection for any novel feature or idea described herein and/or illustrated in the drawings, whether or not emphasis has been placed thereon.

We claim:

1. An ostomy pouch comprising pouch walls joined to form a pouch for receiving fluids from a stoma, a pressure relief valve and a deodorising filter, each at least partly within said pouch, the deodorising filter being non-overlapping and offset from the pressure relief valve, the deodorising filter and the pressure relief valve being mounted on a sub-envelope within the pouch which defines a buffer chamber between the deodorising filter and the pressure relief valve, the pressure relief valve including a fixed case member having a valve seat and a diaphragm capable of seating and unseating on said valve seat so as to close and open said pressure relief valve automatically in response to a gas pressure differential across the diaphragm, said case member at least partly surrounding and protecting said valve seat and diaphragm.

2. The ostomy pouch according to claim 1, wherein the deodorising filter is spaced from the pressure relief valve.

* * * * *